United States Patent
Schieber

(10) Patent No.: US 11,865,085 B1
(45) Date of Patent: Jan. 9, 2024

(54) DEOXYCHOLIC ACID INJECTIONS FOR SNORING AND OBSTRUCTIVE SLEEP APNEA

(71) Applicant: Andrew Schieber, Tustin, CA (US)

(72) Inventor: Andrew Schieber, Tustin, CA (US)

(73) Assignee: Andrew Schieber, Tustin, CA (US)

( * ) Notice: Subject to any disclaimer, the term of this patent is extended or adjusted under 35 U.S.C. 154(b) by 0 days.

(21) Appl. No.: 17/725,970

(22) Filed: Apr. 21, 2022

Related U.S. Application Data

(60) Provisional application No. 63/177,582, filed on Apr. 21, 2021.

(51) Int. Cl.
*A61K 31/047* (2006.01)
*A61K 9/00* (2006.01)
*A61P 11/00* (2006.01)

(52) U.S. Cl.
CPC .......... *A61K 31/047* (2013.01); *A61K 9/0019* (2013.01); *A61P 11/00* (2018.01)

(58) Field of Classification Search
CPC .................................................. A61K 31/047
See application file for complete search history.

(56) References Cited

U.S. PATENT DOCUMENTS

2017/0246032 A1 * 8/2017 Gonzales ................ A61F 7/123

* cited by examiner

*Primary Examiner* — Rei Tsang Shiao
(74) *Attorney, Agent, or Firm* — Christensen, Fonder, Dardi & Herbert PLLC

(57) ABSTRACT

A method for treating obstructive sleep apnea (OSA) and/or snoring that includes the step of administering to a tissue of a mammal an amount of deoxycholic acid. The method includes injecting the deoxycholic acid into a fatty tissue located in the throat, nasal cavity or mouth of the patient so as to reduce a volume of the fatty tissue.

12 Claims, 2 Drawing Sheets

DEOXYCHOLIC ACID INJECTIONS FOR SNORING AND OBSTRUCTIVE SLEEP APNEA

CROSS-REFERENCE TO RELATED APPLICATION

This application claims the benefit of U.S. Provisional Application No. 63/177,582 filed Apr. 21, 2021, the disclosure of which is incorporated by reference herein.

FIELD OF THE INVENTION

The invention relates generally to methods, systems and devices for treating snoring and associated sleep disorder, and more particularly to methods, systems and devices for using deoxycholic acid injections for treating snoring and associated sleep disorder.

BACKGROUND

Roughly 1 in 15 adults in the United States or approximately 18 million people have associated sleep disorder, also called obstructive sleep apnea (OSA) and another 25% of the population or 37 million Americans are at least occasional snorers. Snoring and OSA both occur when tissues in the throat relax and partially or fully obstruct air flow in the throat during normal breathing during sleep. In mild cases this can cause tissue vibrations such as snoring. But in severe cases cause a reduction or pause in breathing. Known systems, devices and treatments may be helpful in addressing OSA, but such known systems, devices and treatments are not always effective.

SUMMARY

Embodiments of the disclosure include methods for treating obstructive sleep apnea (OSA) and/or snoring that includes the step of administering to a tissue of a patient an amount of fat emulsifying or dissolving drug. The fat emulsifying or dissolving drug in an embodiment comprises deoxycholic acid, which is a naturally-occurring acid of the human body. The method includes injecting the drug in liquid or gel form multiple times into a fatty tissue located in the throat, nasal cavity or mouth of the patient so as to reduce a volume of the fatty tissue.

Embodiments of the invention also include a specialized injection device with a curved catheter having a needle tip, and systems including the injection device.

BRIEF DESCRIPTION OF THE DRAWINGS

The present invention will become more fully understood from the detailed description given herein below for illustration only, and thus not limitative of the present invention, wherein.

Figure 1A:
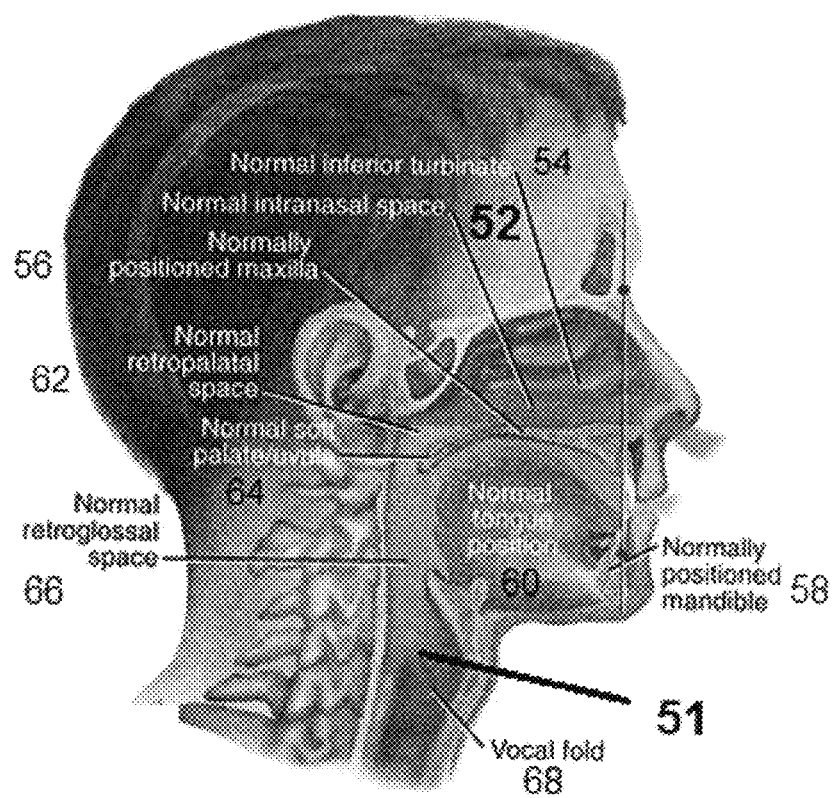
FIG. 1A is a stylized diagram of a normal human head, depicting in cross section, various anatomical features relevant to the invention.

While the embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Referring to FIG. 1A, various anatomical features of the head and throat of a human not experiencing obstructive sleep apnea (OSA) is depicted. FIG. 1A depicts the non-affected or normal anatomical features of a human, including: throat (pharynix) 51, normal intranasal space 52, 54 normalinferior turbinate 54, normally-positioned maxilla 56, normally-positioned mandible 58, normally-positioned tongue 60, normal retropalatial space 62, normal soft palate/uvula 64, normal retroglossal space 66, and vocal fold 68.

Figure 1B:
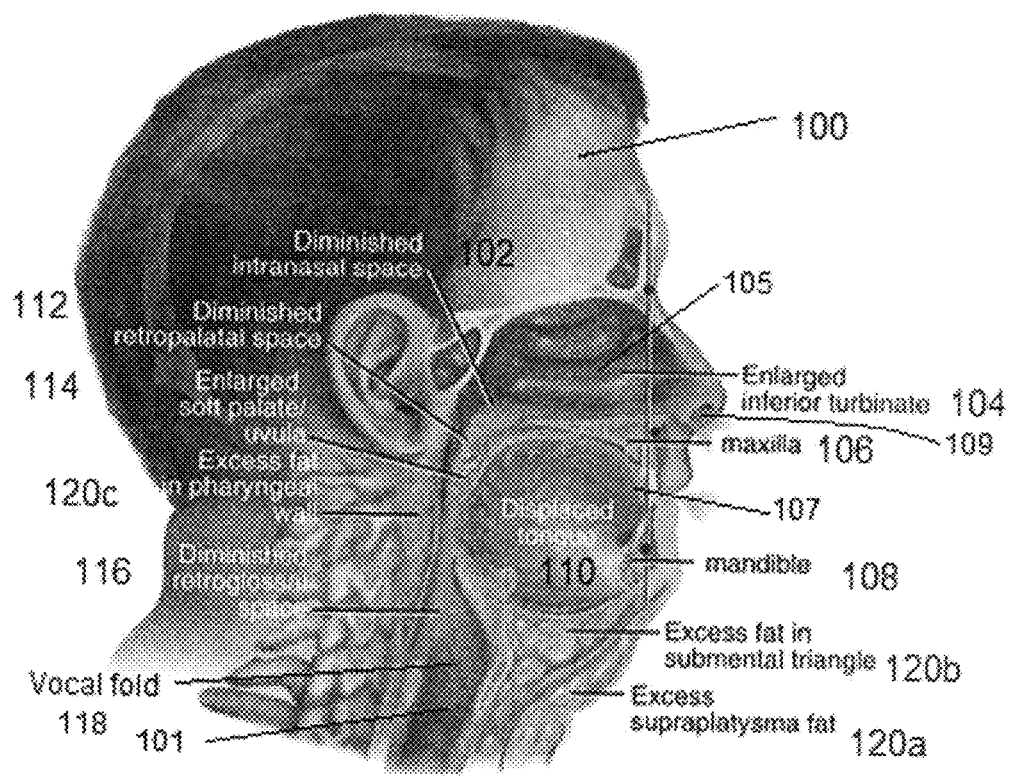
FIG. 1B is a stylized diagram of a human head of a patient affected by OSA, depicting in cross section, various anatomical features relevant to the invention.

In contrast, and referring to FIG. 1B, various affected anatomical features of the head and throat of human patient 100 that may be experiencing obstructive sleep apnea (OSA) is depicted. Patient 100 with OSA will typically experience diminished airway passages in throat (pharynx) 101 and nasal cavity 105, and other symptoms as depicted, including diminished intranasal space 102, hypertrophic inferior turbinate 104, hypoplastic maxilla 106, hypo plastic mandible 108, displaced tongue 110, diminished retropalatial space 112, enlarged soft palate/uvula 114, diminished retroglossal space 116, and excess fats 120, including excess supraplatysma fat 120a, excess fat 120b in the submental triangle, and excess pharyngeal fat 120c in the pharyngeal wall.

Obstruction associated with obstructive sleep apnea (OSA) typically occurs when the muscles that control a person's airway relax too much, narrowing throat 101. Further, obesity is a risk factor for OSA due to an increase in pharyngeal fat tissue 120c in the pharyngeal wall of the throat/pharynx 101. Studies have shown a significantly larger pharyngeal fat 120c pad area 122 in patients with OSA. Even regular snoring can be reduced with weight loss which indicates a relationship between pharyngeal fat tissue 120c and airway blockage.

Known treatments for snoring and OSA don't directly address the cause of snoring and OSA, namely excess fat 120. For example, the well-known use of a CPAP machine may be used to create positive air pressure through your nose or mouth 107; oral devices such as mandibular advancement or tongue advancement devices that pull tissues from a patient's airway; or surgery to correct tissue abnormalities such as deviated septum, swollen tonsils or lower jaw position.

Several surgical procedures are being studied such as upper airway stimulation which involves wires that attach to your lung and neck tracks breathing and sends a signal to pulse your airway muscles to contract and keep open. Somnoplasty uses RF energy to tighten the tissue in the back of the throat. UPPP or UP3 is the surgical removal of tissue in the back of the throat. Nasal surgery is used to correct obstructions in your nose including deviated septum. Mandibular or maxillary advancement surgery moves a patient's jawbone and face bones forward to make more room in the back of the throat for breathing.

Other known treatments include a reduction in alcohol or sleeping pills to reduce tissue relaxation, sleeping on a side of the body to reduce impacts from gravity, and use of nasal sprays to reduce nasal congestions. Even general weight loss is known to sometimes have a positive effect by reducing snoring and OSA. However, general weight loss does not target those specific excess fat 120 areas that are often the primary source of OSA, and may not result in notable or sufficient reduction of excess fat 120.

All existing treatments are either extremely invasive such as surgery or dependent on significant lifestyle changes such as weight loss or CPAP machines. These solutions are either expensive or not desired by patients.

In contrast, embodiments of the disclosure involve a simple injection (or series of injections) that can be easily performed in a clinic by a physician with minimal invasiveness. Such embodiments are targeted to specifically reduce excess fats 120, and include methods of using an existing drug molecule 130 that has been shown to reduce fatty tissue, including pharyngeal fat tissue 120, and an apparatus and system to deliver the drug to the pharyngeal fat tissue 120c. Deoxycholic acid injections (marketed as Kybella® by Allergan Sales, LLC, an AbbVie Inc. company of Lake Bluff, IL, USA) has been approved for reduction in neck fat in patients with "double chin". This indication is primarily for aesthetic purposes but has shown efficacy in reducing excess fat in localized regions of the body. Deoxycholic acid 130 (conjugate base deoxycholate), also known as cholanoic acid, Kybella, Celluform Plus, Belkyra, and 3a,12a-dihydroxy-5β-cholan-24-oic acid, is a naturally-occurring bile acid.

Deoxycholic acid 130 is one of the secondary bile acids, which are naturally-occurring metabolic byproducts of intestinal bacteria. In the human body deoxycholic acid is used in the emulsification of fats for absorption in the intestine. When injected into submental fat, deoxycholic acid 130 helps destroy fat cells.

Embodiments of the disclosure include methods for injecting deoxycholic acid 130, or other fat-emulsifying or fat-dissolving drugs, into throat 101 tissue, including into pharyngeal fat tissue 120c, tongue 110 fat tissue or other tissues in throat, sinus or nasal cavity 102, including excess supraplatysma fat 120c and excess fat 120b in the submental triangle, that affect narrowing airways during breathing. The drug 130 will reduce fat tissue 120 volume in the local tissues and subsequently open the airways of throat 101 for breathing.

Proper injections of deoxycholic acid 130 occur by delivering small volumes of the drug over an array of an injection site the tissue area. In an embodiment, drug 130 may be in a solution of liquid or gel such that the delivered drug 130 solution or gel could have varying concentrations of drug 130, depending on desired effect. The injections are localized and effect only local tissues. Over several treatments, fat tissue is emulsified and absorbed by the body. Once the fat tissue has been reduced in throat 101, a reduction in snoring and OSA would be expected. Since the fat 120 reduction is localized, no other impacts of the drug 130 is expected.

Figure 2:
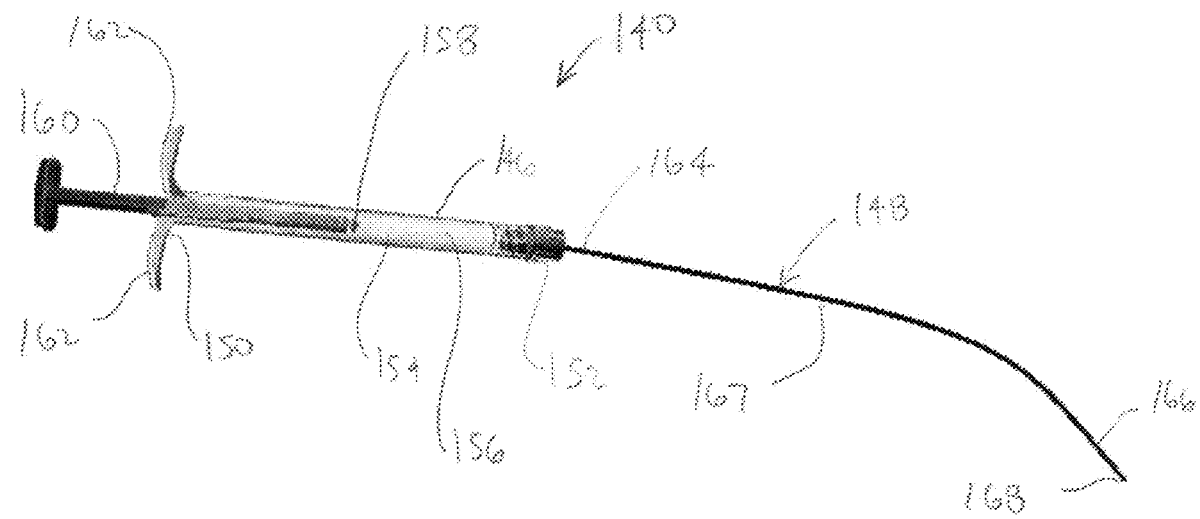
FIG. 2 is a stylized diagram of an OSA treatment system and device, according to an embodiment of the disclosure.
Figure 3:
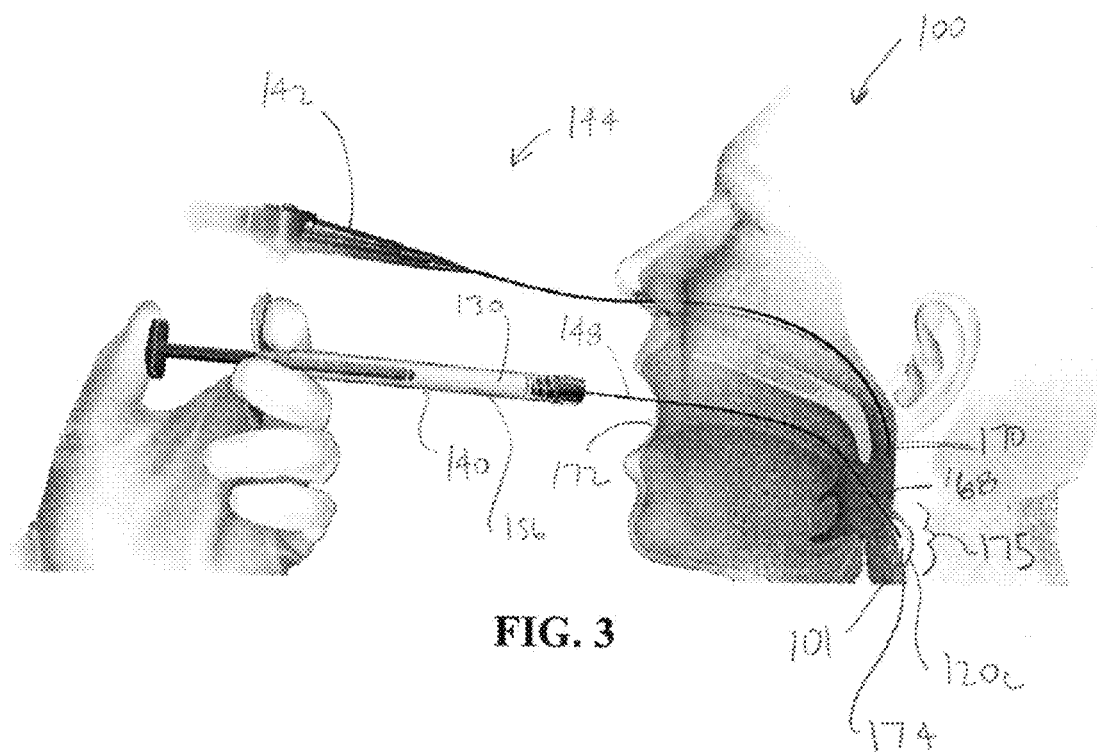
FIG. 3 is a stylized diagram of an embodiment of a OSA treatment system as used to treat a patient with OSA.

Referring also to FIGS. 2 and 3, embodiments of the disclosure include a specialized injector device 140 for delivering the injections to the correct tissue location. Injector device 140 may also be used in conjunction with viewing device 142 to form OSA treatment system 144.

In an embodiment, injector device 140 comprises syringe portion 146 and needle or catheter 148. In an embodiment, and as depicted syringe portion 146 includes proximal end 150 and distal end 152, barrel portion 154 defining barrel chamber 156 for containing a fat emulsifier or dissolver 130 in liquid or gel form, plunger 158, plunger rod 160, and gripping portions 162.

Plunger 158 is located within barrel portion 154 in barrel chamber 156 and is connected to or in contact with plunger rod 160. Gripping portions 162 are located at proximal end 150, and needle 148 is connected to distal end 152 of barrel portion 154.

As described further below, needle 148 is relatively long, and hollow, includes proximal end 164, distal end 166 and main or body portion 167. Proximal end 164 is connected to distal end 152, and distal end 166 comprises tip 168. Needle 148 is in fluid communication with barrel chamber 156 and its contents.

Generally, a user grips barrel portion 154 and its gripping portions 162 and pushes an end of plunger rod 160 that is outside of barrel chamber 156, forcing plunger rod 160 and plunger 158 in a direction from proximal end 150 toward distal end 152, forcing fat emulsifier or dissolver 130 through needle 148 and out of a port of tip 168.

Access to the proper area of throat 101 is accomplished using the specialized micro-volume injector device 140 along with the specialized needle 148 with tip 168 to ensure the proper location and depth of delivery. Injector device 140 could include a traditional mechanical syringe, motorized syringe, spring-driven syringe or a gas-powered micro-volume injector. The delivery volumes of drug (fat emulsifier or fat dissolver) 130 may vary depending on the amount of fat tissue and the concentration of the drug 130 being delivered. In an embodiment, injection device 140 could be configured to deliver a very small volume of drug 130 ranging from 0.1 µL to 10 mL of fluid for each injection. For larger injection areas and/or a larger quantity of tissue, the relative volume of drug 130 may be higher as compared to smaller areas or quantities of fat tissue to be injected. The volume of chamber 156 is determined in part by the number of injections intended to be given times the volume per injection. In an embodiment, an injection site may be injected many times, such as from 1 to 50 times.

In an embodiment, needle 148 of micro-injector device 140 may comprise a catheter with a needle tip 168, or a long flexible needle. Such needle tips 168 may be micro-gauge tips to ensure precision delivery. Needle or catheter 148 may also include ergonomic curvature to provide access to areas of the throat that may not be possible with traditional syringes. This includes long or curved sections of the needle tip, depth control needle tips or extended grip plunger to provide the injector the proper control during the injection. In an embodiment, needle or catheter 148 has a "memory" so as to hold a predefined curvature configured for precision location of tip 166 in throat 101. The curved shape of catheter or needle 148 may be configured to match a contour and curvature of a pathway starting at the opening of the mouth 107 of the patient, traversing through mouth 107 and throat 101 of patient 100 and ending at the fatty tissue 120.

Referring specifically to FIG. 3, OSA treatment system 144 is depicted in use. As briefly described above, OSA treatment system 144 includes injector device 140 and viewing device 142. In an embodiment, OSA treatment system 144 also includes fat emulsifier or dissolver 130, which may be or comprise deoxycholic acid, located in chamber 156.

In an embodiment, viewing device 142 may comprise one or more of a light source, camera or endoscope with an insertion end 170 configured for insertion into and through the nasal passages and into throat 101. In one such embodiment, viewing device 142 may comprise an endoscope such as, or similar to a laryngeal endoscope. Embodiments of endoscopes for insertion into and through the nasal passages and into the throat are known.

Still referring to FIG. 3, embodiments of the disclosure include methods of treating snoring and OSA by injecting fat emulsifying or dissolving compound or drug 130, which may be deoxycholic acid, into fat tissue 120 in a patient's throat. Embodiments of such treatment methods may include one or more of the following steps:

Step 200: Inserting insertion end 170 of light source or endoscope 142 through the nasal passages 109 of a patient 100 and into the patient's throat 101. Alternatively, insertion end 170 of light source or endoscope 142 may be inserted through mouth 107 of patient 100 into throat 101 and located near injection area 175 that may include areas of fatty tissue 120 and possibly adjacent tissue in throat 101.

Step 202: Activating the light source or endoscope 142 such that a user of endoscope 142 is able to view an injection area 175 of an excess fat tissue 120;

Step 204: Identifying a fat tissue 120 in throat 101 and intended injection site 174 of excess fat tissue 120 (as depicted, excess fat tissue 120 is excess pharyngeal fat 120c). It will also be understood that although injection of pharyngeal fat 120c is depicted and described, other excess fat tissues 120 in other areas of the throat 101, nasal cavity 105 and mouth 107 may be identified and treated.

Step 206: Inserting distal end 166 of needle 148 through mouth 107 of patient 100 and into the patient's throat 101;

Step 208: Piercing excess fat tissue 120 with needle end 168 at an injection site in an injection area 175;

Step 210: Activating injection device 140 to cause a first small volume of fat emulsifying or dissolving compound 130 to flow out of chamber 156, through needle 168, out of needle end 168 and into excess fat tissue 120. A volume per injection varies as described above, and in an embodiment may range from 0.1 µL to 10 mL of fluid for each injection.

Step 212: Removing needle tip 168 from excess fat tissue 120;

Step 214: Inserting needle tip 168 into excess fat tissue 120 at another injection site in the injection area 175, and near the prior injection site;

Step 216: Activating injection device 140 to cause a second small volume of fat emulsifying or dissolving compound 130 to flow out of chamber 156, through needle 168, out of needle end 168 and into excess fat tissue 120;

Step 218: Repeating steps 212, 214 and 216 as needed. The number of times that steps 212 to 216 are done depend on the quantity of excess fat tissue 120, size and accessibility of injection area 174, concentration of injected drug 130, and so on. In an embodiment, excess fat tissue 120 at an injection site 174 may be injected from 1 to 20 times; in another embodiment, injections range from 1 to 30 times.

Step 220: Remove injection device 140 with needle 148;
Step 222: Remove viewing device 142.

The above-described methods, devices and systems for treating snoring and OSA provide alternative solutions to OSA that directly target and threat the cause of OSA by dissolving excess fat in the throat, in a manner that is superior when compared to the use of airway-opening devices, surgery and general weight loss.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A method for treating obstructive sleep apnea (OSA) and/or snoring, comprising the step of administering a plurality of injections to multiple portions of a fatty tissue located in the throat of a mammal an amount of deoxycholic acid.

2. The method of claim 1 wherein the amount of deoxycholic acid administered is sufficient to reduce the fatty tissue volume.

3. The method of claim 1 wherein the amount of deoxycholic acid administered is sufficient to enlarge an airway defined by the fatty tissue.

4. The method of claim 1 wherein the amount of deoxycholic acid administered is sufficient to destroy fat cells in the fatty tissue.

5. The method of claim 1 wherein the amount of deoxycholic acid administered is sufficient to emulsify fat cells in the fatty tissue.

6. The method of claim 1, wherein the fatty tissue is pharyngeal fatty tissue.

7. The method of claim 1, wherein the plurality of injections ranges from two injections to ten injections.

8. The method of claim 1, wherein a volume of fluid for each of the plurality of injections is in a range of 0.1 µL to 10 mL of fluid.

9. The method of claim 8, wherein a volume of deoxycholic acid in the fluid is in a range of 0.1 µL to 10 mL.

10. The method of claim 1, wherein injecting the deoxycholic acid into the fatty tissue comprises injecting the deoxycholic acid into a fatty tissue at a first location of the throat and injecting the deoxycholic acid into a fatty tissue at a second location of the throat.

11. The method of claim 1, wherein the first location is the pharyngeal wall and the second location is the submental triangle.

12. A device for treating snoring and/or OSA, comprising:
an injector device including a syringe portion and a catheter portion, the syringe portion defining a chamber for containing a fluid, and the catheter portion defining a lumen in fluid communication with the chamber, and including a body portion and a needle tip at a distal end of the body portion for insertion into a fatty tissue of the throat, the body portion of the catheter forming a curved shaped configured to match a contour of the mouth and throat of a patient, and to contact the fatty tissue in the throat at the needle tip.

* * * * *

UNITED STATES PATENT AND TRADEMARK OFFICE
CERTIFICATE OF CORRECTION

| | | |
|---|---|---|
| PATENT NO. | : 11,865,085 B1 | Page 1 of 1 |
| APPLICATION NO. | : 17/725970 | |
| DATED | : January 9, 2024 | |
| INVENTOR(S) | : Schieber | |

It is certified that error appears in the above-identified patent and that said Letters Patent is hereby corrected as shown below:

On the Title Page

Column 1, Item (51), under "Int. Cl.", Lines 2-3, delete
"*A61K 9/00* (2006.01)
*A61P 11/00* (2006.01)".

In the Specification

In Column 2, Line 17, delete "(pharynix)" and insert -- (pharynx) --, therefor.

In Column 2, Line 17, after "52,", delete "54".

In Column 2, Line 18, delete "normalinferior" and insert -- normal inferior --, therefor.

In Column 2, Line 20, delete "retropalatial" and insert -- retropalatal --, therefor.

In Column 2, Line 30, delete "retropalatial" and insert -- retropalatal --, therefor.

In Column 2, Lines 32-33, delete "supraplatysma" and insert -- supraplatysmal --, therefor.

In Column 3, Line 18, delete "pharyingeal" and insert -- pharyngeal --, therefor.

In Column 3, Line 42, delete "supraplatysma" and insert -- supraplatysmal --, therefor.

Signed and Sealed this
Twenty-ninth Day of April, 2025

Coke Morgan Stewart
*Acting Director of the United States Patent and Trademark Office*